United States Patent [19]

Barsky et al.

[11] Patent Number: 5,508,188
[45] Date of Patent: Apr. 16, 1996

[54] METHOD OF GROWING CELLS IN A MAMMAL

[75] Inventors: Sanford H. Barsky; Mark Sternlicht, both of Los Angeles, Calif.

[73] Assignee: The Regents of the University of California, Oakland, Calif.

[21] Appl. No.: 184,720

[22] Filed: Jan. 21, 1994

[51] Int. Cl.$^6$ ............................... C12N 5/00; C12N 5/02
[52] U.S. Cl. ............................... 425/240.2; 435/240.1; 435/240.25
[58] Field of Search ............... 424/93.2; 435/172.3, 435/240.1, 240.2, 240.25

[56] References Cited

U.S. PATENT DOCUMENTS 4,829,000 5/1989 Kleinman et al. .
5,158,874 10/1992 Kleinman et al. .

FOREIGN PATENT DOCUMENTS

WO915245 10/1991 WIPO .

OTHER PUBLICATIONS

Barsky & Sassoon, "Sclerosing Adenosis of the Prostate as a Cause of Very High PSA Levels" J. Urological Pathology (1993) 1: 313–331.

Ellis & Wiscovitch, "Basal Cell Adenocarcinomas of the Major Salivary Glands," Oral. Surg. Oral Med. Oral Pathol. (1990) 69: 461–469.

Barsky et al., "Two Human Tumors with High Basement Membrane Producing Potential," Cancer (1988) 61: 1798–1806.

Caselitz et al., "Basal Membrane Associated Substances in Human Salivary Glands and Salivary Gland Tumours.," Path. Res. Pract. (1988)183:386–394.

Chaudhry et al., "Histogenesis of Adenoid Cystic Carcinoma of the Salivary Glands," Cancer (1986) 58: 72–82.

Primary Examiner—Jacqueline M. Stone
Assistant Examiner—Deborah Crouch
Attorney, Agent, or Firm—Bertram I. Rowland

[57] ABSTRACT

Human basement membrane matrix is provided, produced by a novel tumorigenic cell line, where the basement membrane can be used for the growth of a variety of cells, in culture and in vivo. Other cell lines are provided, which may serve to evaluate in vivo the response of tumorigenic cells to various agents, including basement membrane. The basement membrane finds use in allowing the growth of cells in culture and in vivo, particularly cells which are otherwise refractory to xenografting.

3 Claims, No Drawings

METHOD OF GROWING CELLS IN A MAMMAL

TECHNICAL FIELD

The field of this invention relates to basement membranes and extracellular matrices and their production.

BACKGROUND

Basement membranes are ubiquitous structures which are thought to be synthesized by several normal cell types including epithelial, endothelial, smooth muscle, Schwawn cells, and their derivatives. However, the transformed malignant counterparts of these cells, carcinomas and sarcomas, generally loose their ability to synthesize basement membranes and instead acquire basement membrane-degradative properties via the secretion of different families of proteases including metalloproteinases, serine proteinases and thiol proteinases.

Because of the almost universal inability of human tumors to produce basement membranes, studies designed to investigate tumor cell interactions with basement membranes have relied heavily upon utilizing matrix derived from the unusual non-metastasizing Engelbreth-Holm, Swarm ("EHS") tumor. The EHS tumor matrix is rich in laminin, type IV collagen, nidogen and heparin sulfate proteoglycan, as well as the small matrix glycoprotein BM-40. These molecules have been extracted individually and as an unfractionated extract which reconstitutes to form a three-dimensional gel ("Matrigel" containing entrapped growth factors. This reconstituted basement membrane has been used extensively to study cellular differentiation, tumor cell invasion, angiogenesis and tumorigenicity. The coinjection of tumor cells and matrigel enables the in vivo growth of several otherwise non-tumorigenic cells and greatly stimulates the growth of a wide variety of primary and established tumor cells of both human and murine origin. However, matrigel has failed to support the growth of many primary human cancers, including prostatic and breast carcinoma. It is therefore of substantial interest to develop basement membrane compositions of human origin having human proteins and factors for the investigation of human tumors and to act as a source of basement membrane components.

RELEVANT LITERATURE

Barsky et al. (1988) Cancer 61: 1798–1806 screened a series of human tumors by anti-laminin ELISA and discovered salivary gland adenold cystic carcinoma to exhibit the highest amounts of human native extracellular matrix molecules. See also Ellis and Wiscovitch (1990) Oral Surg. Oral Med. Oral Pathol. 69:461–469 and Chudhry et al. (1986) Cancer 58:72–82. Myoepithelial cells are reported to be a rich source of basement membrane material in vivo and are likewise thought to be the source of basement membrane material in these tumors. Caselitz et al. (1988) Path. Res. Pract. 183:386–394: Chudhry, 1986, supra. U.S. Pat. Nos. 4,829,000 and 5,158,874, as well as PCT/US91/02122 (WO91/15245) described the preparation of Matrigel and its use in determining metastatic potential of tumor cells and growing tumor cells.

SUMMARY OF THE INVENTION

A human basement membrane composition ("Humatrix") is provided, which comprises the protein components of human basement membrane in a three-dimensional scaffold. Humatrix finds use in the growth of human tumor cells, evaluation of metastatic potential of tumor cells and as a source of the purified protein components. Humatrix can be obtained by extraction of the basement membrane matrix from a xenograft of a salivary gland basal cell adenocarcinoma. A related tumor cell composition finds use in evaluating tumor characteristics associated with formation of basement membrane and production of basement membrane degrading enzymes.

In referring to "Humatrix" is intended a human basement membrane-like/extracellular matrix composition comprising at least the major constituents of the naturally occurring human basement membrane, where various growth factors may or may not be present. The ratios of the components will be about +/−10% from the average of the naturally occurring tumoral basement membrane and extracellular matrix, again with the possible exception of type IV collagen. The composition will at least comprise heparan sulfate proteoglycan, chondroitin sulfate proteoglycan, type I and IV collagen, laminin, and nidogen/entactin, usually also including fibronectin and a novel 55 kDa glycoprotein.

DESCRIPTION OF THE SPECIFIC EMBODIMENTS

In accordance with the subject invention, compositions are provided having combinations of human basement membrane proteins ("Humatrix"), which are present as a three-dimensional scaffold structure, analogous to natural basement membranes. Depending upon the method of isolation, the composition has in descending concentration heparan sulfate proteoglycan, chondroitin sulfate proteoglycan, fibronectin, type I collagen, nidogen/entactin, type IV collagen (varies from about 1% of the naturally occurring amount to greater than about 100% of the naturally occurring amount, preferably about +/−10% of the naturally occurring amount), laminin and entrapped growth factors including TGF-β, EGF, bFGF, IGF-1, IGF-2, PDGF. These growth factors may be extracted from the gel, in whole or in part, their amounts may be enhanced, or additional factors added such as interleukins 1–15, colony stimulating factors, such as G-, M- or GM-; interferons, e.g. α, β or γ, erythropoietin, LIF, c-kit ligand, bone morphogenetic factors, NGF, or other factors that may find use in a particular application. For the most part, the entrapped growth factors will be present in a range of about 1 to 2 weight percent of the composition. Other factors, such as purified exogenous growth factors, particularly as described above, may be added to provide from about 2 to 5 weight percent, depending on the particular factor, the presence of other factors, the context in which Humatrix is being used, or the like.

For the most part, the heparan/chondroitin sulfate proteoglycan will be present in from about 15 to 35, more usually 20 to 30 weight %; fibronectin will be present in from 10–20% weight, the type I collagen will be present in from about 1 to 15 weight %, usually 2 to 10 weight %; the type IV collagen will be present in from about 1 to 15 weight %, usually from about 2 to 10 weight %; laminin will be present in from about 1 to 15 weight %, usually from about 2 to 10 weight %; nidogen/entactin will be present in from about 7.5 to 12.5 weight %, usually about 10 weight %; other minor proteins, such as BM90/fibulin, bamin, and BM40 will be present in from about 0.5 to 5 weight %, generally being present in total in from about 3 to 7 weight %, more usually a total of about 5 weight %. The remaining portion of the composition will include the 55 kDa protein and unknown components and will comprise not more than about 40 weight %, usually not more than about 30 weight %, and preferably not more than about 30 weight %.

The subject composition will vary with the extraction method employed. With either method there will usually be less than about 40 weight % comprising presently unreported components. Included in this group is the 55 kDa protein, which is characterized as having a 55 kDa molecular weight as determined by SDS-PAGE, glycosylated as evidenced by alcian blue staining; traveling as a single band under reducing and non-reducing conditions in gel electrophoresis actively synthesized by HMS-X as determined by $^{35}$S-methionine labelling; absent in Matrigel and EHS tumor extracts, but present in other related salivary gland tumors: an adenoidcystic human xenograft and a human pleomorphic adenoma, tumors which produce similar extracellular matrix:; absent from normal human tissue, including known sources of basement membrane components, such as placenta and kidney; and associated with the Humatrix fraction upon extraction with 2 M urea or guanidinium-HCl, but not in the 3.4 M NaCl extract; and produced by HMS-X, but not HMS-1.

Depending upon the manner of extraction, certain components in the Humatrix may vary. While for the most part, the sulfate proteoglycans and fibronectin will remain in about the same range, the type I collagen will on the average be in the range of about 2–5 weight % when extracting with urea/gdn-HCl, while about 5–10 weight % when using pepsin hydrolysis; the type IV collagen will generally be on the average in the range about 5–10 weight %, with urea/gdn-HCl, and about 2–5 weight % with pepsin hydrolysis; laminin will be present on the average in about 2–10 weight % with urea/gdn-HCl, and about 5–10 weight % with pepsin hydrolysis. The other characterized compounds will fall within the same ranges regardless of the manner of extraction. However, as already indicated the ranges may be changed by the addition of any of the components, although in the presence of the various components in solution, there appears to be a preferred ratio of the various components in the matrix.

It is found that the major basement membrane molecules (type IV collagen, laminin, nidogen and heparan sulfate proteoglycan) interact with one another and coprecipitate when combined in vitro. Depending upon the manner of isolation of Humatrix, type IV collagen may be underrepresented in the Humatrix composition. In order to provide for representative amounts of type IV collagen, the tumor bearing host must be rendered lathyritic, for example, with β-aminopropionitrile and a reducing agent employed during the extraction of Humatrix. In the absence of such agent, lower levels of type IV collagen are present. It is further found, that the relative proportions (plus or minus 25% of the average proportion) of the reconstituted matrix molecules remains constant with various manipulations, indicating that the molecules interact in a stoichiometric manner. Humatrix resembles Matrigel in its overall structure and appearance at a grossly visible level, but may differ from Matrigel at a molecular interactive level.

Humatrix is preferably stored at −20° C., being a liquid at 4° C. and undergoes gelation at about 25°–37° C.

The subject compositions are biologically active in being able to support tumor growth, both in vitro and in vivo. Particularly, the subject compositions can be used with fastidious human tumors, both primary and cell lines. It is known that human breast carcinomas and prostatic cancers are particularly difficult to grow in vitro and as xenografts.

The subject compositions can also be used for the growth and differentiation of a variety of cells. Humatrix is particularly useful for the growth of epithelial cells and can provide for cell adhesion, growth and differentiation of a multiplicity of cells, including neurons, hepatocytes, sertoli cells, hair follicles, thyroid cells, and the like.

"HMS-X has been deposited with the ATCC, 12301 Parklawn Dr., Rockville, MD 20852 USA, on May 25, 1995 and given the accession no. CRL 11899. In addition, HMS-1 has been deposited with the above mentioned depository on Jan. 12, 1995 and given the accession no. CRL 11792". These cell lines are all derived from a human parotid basal cell adenocarcinoma, a subtype of adenoidcystic carcinoma. HMS-1 is established directly from the patient's tumor in keratinocyte growth media (KGM) supplemented with recombinant epidermal growth factor and bovine pituitary extract. It is mycoplasma-free, as evidenced by direct culture and indirect Hoechst DNA staining, as well as by electron microscopy. The line exhibits immortality in a stable phenotype, having been passed unchanged for over 100 passages with a population doubling time of approximately 24 hours. Phase contrast microscopy reveals polygonal cells with prominent nucleoli, which grow independent of one another until a confluent monolayer is formed. The cells are immunoreactive for low molecular weight cytokeratins and smooth muscle actin indicating their myoepithelial nature. Approximately 30% of the cells show positive immunostaining for laminin and type IV collagen, suggesting cell cycle-dependent expression of these molecules. Ultrastructural examination reveals microvilli and parallel arrays of microfilaments (thin filaments), dual structures supportive of a myoepithelial phenotype. Monolayer cultures in KGM reveal the presence of a scant basal extracellular electron dense matrix and the complete absence of cell-to-cell attachments (desmosomes).

When HMS-1 is grown in serum-containing media, HMS-1 cells undergo growth arrest at lower cell density, a change in growth pattern to island morphology, and epithelial differentiation which is reflected in the acquisition of numerous desmosomes. The cell line eventually undergoes terminal differentiation in serum after several doublings.

Chromosome analysis carried out by Giemsa-band staining of metaphase spreads at different passages, from 2 to 55 reveal an essentially diploid modal chromosome count of 46–47 (Range, 44–50). Common karyotypic changes are the loss of chromosomes 6 and 22, an abnormal chromosome 8q and the acquisition of a rearranged marker chromosome, t(6;9) (p11.2; pl 3). There is also an apparent gain of an extra chromosome during early passages. DNA ploidy analysis of several early and late passages by flow cytometry confirms the stable diploid nature of the line. The tumor xenograft, HMS-X can be initiated by direct subcutaneous implantation of tumor fragments at appropriate cites of an immunocompromised mammalian host. Conveniently, murine hosts may be employed such as C.B/17 scid/scid mice, nude mice, rag-1$^-$ and/or rag-2$^-$ mice, chemically immunosuppressed mice, irradiated mice, or the like. For producing large amounts of the Humatrix composition, it may be desirable to use larger animals, such as rats, rabbits, or other laboratory animals which can conveniently be grown under controlled conditions. HMS-X increases on average 1 mm in diameter every two weeks.

The original surgical specimen providing HMS-1 and HMS-X was a white to tan, multinodular mass exhibiting cylindromatous and cribriforming histologic patterns with abundant acellular matrix deposits, as well as squamous metaplastic changes within invasive islands. The transplanted xenograft exhibited a gross appearance similar to that of the original tumor. The xenograft retained an abundant eosinophilic extracellular matrix which stained strongly with alcian blue and periodic acid-schiff (PAS) stains. The PAS positivity was diastase-sensitive suggesting the presence of glycosylated matrix molecules other than mucin, e.g. proteoglycans. The extracellular matrix, which comprised better than 50% of the tumor volume, also exhibited strong immunoproxidase staining for laminin. Electron microscopy reveals tumor cell islands surrounded by an abundant ground substance-like matrix which lacks periodic cross-banded fibers and resembles the ultrastructural appearance of both Matrigel and the native EHS tumor matrix.

DNA fingerprint profiles show identity for the xenograft and three passages of the cell line, demonstrating a novel band pattern differing from that of HeLa cells and a negligible DNA contribution from murine cells. Flow cytometric analysis confirms the diploid nature of the original surgical specimen as well as early and late tumor transplant generations.

Gene expression of most matrix molecules is considerably greater for HMS-X than for HMS-1 and HMS-XC, a cell line subsequently derived from HMS-X. Fibronectin gene expression shows the opposite pattern of gene expression, being 20-fold greater than HMS-1 than HMS-X. While the effects of serum on the extracellular matrix gene expression of HMS-1 mimic to some extent the expression noted in HMS-X, the expression is still both quantitatively and qualitatively different. The expression by HMS-1 of some matrix genes remains substantially unchanged by serum.

The tumorigenicity of HMS-1 appears to be matrix dependent in that the cell line did not form tumors in athymic (nude) or SCID mice, yet it serially transplanted xenograft HMS-X was 100% tumorigenic. The HMS-XC cell line derived from HMS-X was also non-tumorigenic, despite being injected after only a single in vitro passage. The tumor cells failed to grow xenografts after removal of the supporting extracellular matrix from the explant by mechanical enzymatic dissociation and subsequent reinjection of the washed cells, despite their ability to grow in culture. This observation indicates that the cell lines are obligately matrix dependent for their tumorigenicity. While Matrigel exerts a profound effect on the growth and morphogenesis of HMS-1, Matrigel is ineffective in stimulating the tumorigenicity of HMS-1.

Humatrix is prepared at continually reduced temperature (4° C.) by repeated homogenization and centrification of HMS-X in a high salt solution containing protease inhibitors followed by overnight extraction in either a 6 M urea, 2 M guanidinium-HCl (gdn-HCl) buffer; or in a pepsin/acetic acid mixture. Salt concentrations will generally range from about 3.2 to 3.4 M and the tumor explant will generally be homogenized at a ratio of 2 ml to 1 g in the salt solution. The final pellet obtained from the high salt extraction would generally comprise about from 40 to 70% of the original explant. This pellet will be mixed with 0.5 ml urea/gdn-HCl/g of starting material or 5 ml 0.5 N acetic acid per g of starting material with 160 μl of freshly prepared 50 mg/ml pepsin in 0.01 M HCl per g of starting material. The extraction process may be repeated, the supernatants combined and dialyzed against dilute aqueous chloroform (usually about 0.2 to 1%, more usually about 0.5% chloroform) using a dialysis membrane having a cutoff of 5–10 kDa. The temperature of the dialysis will generally be at about 0° to 10° C., usually 4° C., and the dialysis will be carried out for about 8 to 12 hr. After the dialysis with dilute aqueous chloroform, the supernatant will ordinarily be dialyzed against physiologic medium to make the product physiologically acceptable. The resulting product, Humatrix, may then be stored at –20° C.

The subject human best basement membrane composition can replace Matrigel for its uses, particularly for human cells. It can be used as a coating for lab wear, where cells are to be grown in culture. It can be employed in a variety of tumor cell invasion assays (Taniguchi et al. (1989) Cancer Research 49:6738; Terranova et al. (1986) Proc. Natl. Acad. Sci. USA 83:465; Albini et al. (1987) Cancer Research 47:3239; and Hendrix et al. (1987) Cancer Letters 47:3239). The subject composition can support peripheral nerve regeneration, differentiation of epithelial cells, and may serve as a substrate for the study of angiogenesis. The subject membrane may be coated in a variety of ways where the Humatrix may be coated as a thin layer on a gel for plating cells on top of the gel, as a thick layer to allow for growth of cells within a three-dimensional matrix, or a thin coat, without gel, to provide a complex protein layer upon which cells may be grown. Generally, Humatrix will be used at a protein weight percent in the range of about 1 mg to 3 mg/ml, depending on the method of extraction. The subject composition may be used with cultures which are serum-free or contain serum.

The subject compositions can be used with cells for investigating the mechanisms of cell attachment, embryogenesis, morphogenesis, cell growth and differentiation, immunologic modulation, invasion and metastasis, as well as the role the basement membrane and extracellular matrix may play in a variety of diseases, as a result of pathogenesis, genetic defect, or the like. The subject membrane may also be used to investigate binding of a wide variety of factors to the basement membrane, the effect of the basement membrane on the activity of such factors, and the like.

The subject composition may be used in conjunction with a variety of cells to enhance the growth of the cells as xenoplants. All that is required, is that the cells, particularly human cells, are mixed in about a 1:1 volume ratio of cells to Humatrix and then injected into an appropriate host, particularly an immunocompromised host as described above. Thus, a wide variety of cells can be rapidly grown in an appropriate host.

Of interest, is the use of SCID-hu mice as described in EPA 88/312222.8; PCT/US91/02938; and EPA 91/113061.5. By providing for human tissue in the SCID-hu mouse, one can determine the metastatic potential of cells by determining whether the depot of tumor cells in the Humatrix composition metastasize to the human tissue. A wide variety of human tissue may be employed, such as bone marrow, bone marrow equivalent (see PCT/US93/04264), epithelial tissue, gut, pancreas, neural tissue, and the like.

In addition, one can study the effect of various agents on the growth of the tumor cells and the metastasis of the tumor cells in culture and in vivo. Thus, drugs may be employed for introduction into a culture medium or into a host at various concentrations, to determine the activity of the drug and its activity profile.

The following examples are offered by way of illustration and not by way of limitation.

EXPERIMENTAL

Materials and Methods

High molecular weight DNA was extracted from HeLa cells, HMS cells, HMS tumor, and nude mouse tissue by standard procedures using RNAase A, proteinase K, SDS and phenol (Sambrook et al., 1989, Molecular Cloning: A Laboratory Manual, CSHL, NY). The DNA was digested overnight at 37° C. with 14 units of Hinfl or HaeIII per μg of DNA in the appropriate reaction buffer. Sodium acetate (pH 5.2) was then added to a 0.3 M final concentration and the DNA was precipitated with ethanol. The recovered DNA was redissolved in TE (10 mM Tris, 1 mM EDTA; pH 8.0) and 3 μg of DNA were loaded onto each lane of a 24-cm-long, 1% agarose gel containing 0.3 μg/ml ethidium bromide. HindIII cut γ and HaeIII cut φX174 DNA molecular weight markers were run on both sides of the sample lanes. Electrophoresis was performed at 75 V for 16 hours in 1× TAE electrophoresis, the migration of DNA markers was determined by UV transillumination of the gel. For alkaline Southern transfer, gels were equilibrated in 0.4 N NaOH, 0.6 M NaCl for 30 minutes with agitation, and the denatured DNA was transferred overnight onto Nytran nylon membranes (Schleicher & Schuell, Keene, NH) by Southern capillary transfer in the same buffer. The membranes were neutralized in 5×SSC for 10 minutes and the DNA was immobilized by 254 nm UV crosslinking at 0.12 J/cm$^2$ of filter. Blots were stored desiccated at 4° C. between two sheets of Whatman 3 MM paper and in plastic wrap.

The single-locus hypervariable probe pYNH24 was obtained from American Type Culture Collection (Rockville, MD) in plasmid form (ATCC 57571). HB101 E. coil were rendered competent by suspension in 50 mM CaCl$_2$ and were transformed by standard methods (Sambrook et al., 1989, supra). Transformants were selected on LB agar plates containing 50 μg/ml ampicillin and were confirmed to contain the plasmid by restriction digest analysis of small-scale plasmid preparations. Plasmid was amplified in host E. coil grown overnight in LB culture medium supplemented with 50 μg/ml ampicillin at 37° C. in a gyrating water bath at 225 rpm. Plasmid was then recovered from large-scale cultures by alkaline lysis and was purified by ethidium bromide-CsCl equilibrium centrifugation (Sambrook et al., 1989, supra). The 2.00 Kb insert was excised from pUC18 vector by sequential digestion with HindIII and EcoRI, and was isolated from a 1% low-melting-point agarose gel run in 1×TBE (90 mM Tris-borate, 2 mM EDTA; pH 8.0). Gel slices containing the insert were centrifuged for 5 minutes at 12,000 g and 5 M NaCl was added to yield a 0.3 M final concentration. After 1 hour at room temperature, the gel slices were melted at 65° C. for 10 minutes, and the DNA was extracted twice with 65° C. saturated phenol, further extracted twice with chloroform, precipitated with ethanol, and resuspended in TE. Twenty-five ng of insert were labeled with 50 μCi (3000 Ci/mmol) $\alpha^{32}$P-PdCTP by random priming with a commercially available kit (Random Primers DNA Labeling System; BRL, Gaithersburg, MD). Unincorporated nucleotides were removed from the radiolabeled probe by Sephadex G-50 spun column chromatography over TE Select-D, G-50 columns (5 Prime- 3 Prime, Boulder, CO), The multi-locus hypervariable probe 33.6 and a specific labeling primer were obtained from Cellmark Diagnostics (Germantown, MD). Twenty ng of the probe were labeled with 50 μCi (3000 Ci/mmol) $\alpha^{32}$P-dGTP by primer extension as recommended by the supplier. Unincorporated nucleotides were removed from the radiolabeled probe by Sephadex G-50 spun column chromatography.

For some blots, the multi-locus probe 33.6 was obtained from a recombinant plasmid containing the 720 bp 33.6 DNA fragment. First, the vector pCRll (Invitrogen, San Diego, CA) was sequentially digested with HindIII and EcoRI. The released polylinker fragments were removed using a Select-D G-50 gel filtration column, and the vector was ethanol precipitated and resuspended in TE. Fifty ng of digested vector and 20 ng of 33.6 with EcoRI and HindIII sticky ends (Cellmark Diagnostics) were combined with T4 DNA ligase and the appropriate ligation buffer (Invitrogen), and ligation was allowed to proceed overnight at 12° C. Competent InvαF' E. coli were transformed with 1 μl of the ligation mixture according to the methods outlined by the supplier (Invitrogen). Recombinant clones were selected by ampicillin resistance and interruption of the LacZcα gene which resulted in white colonies on LB agar plates containing 50 μg/ml ampicillin and 1 mg X-Gal. Presence of the recombinant plasmid was confirmed by restriction digest analysis of small-scale plasmid preparations on 1% agarose gels. Plasmid was then recovered from large-scale cultures by alkaline lysis and was purified by pZ523 spun column chromatography according to the methods recommended by the manufacturer (5 Prime- 3 Prime). The 720 bp insert was released from the vector by sequential digestion with HindIII and EcoRI, and was isolated from a 1% low-melting-point agarose gel as described above for the pYNH24 insert. Twenty-five ng of gel isolated insert were labeled by random priming and the radiolabeled probe was separated from unincorporated label as described above.

Nytran filters were placed in glass roller bottles and wetted briefly with deionized water. Nine ml of prewarmed QuikHyb hybridization solution (Stratagene, La Jolla, CA) were added, and the membranes were incubated at 68° C. in rolling hybridization oven for 30 minutes. One mg of sonicated salmon-sperm DNA and 12.5×10$^6$ cpm of $^{32}$P-labeled probe were combined and boiled for three minutes. One ml of prewarmed hybridization solution was then added to the boiled DNA and the mixture was transferred to the roller bottles and hybridization was carried out for 2 hours at 68° C. The membranes were washed twice with 2×SSC, 0.1% SDS at room temperature for 15 minutes with gentle agitation and then once with prewarmed 0.1×SSC, 0.1% SDS at 60° C. for 30 minutes in a rolling hybridization oven. The damp membranes were wrapped in plastic wrap and were exposed to Kodak X-OMAT AR film between two intensifying screens at –60° C. for 1 to 10 days. Blots which were stripped for reuse were washed twice for 15 minutes with near boiling 0.1×SSC, 0.1% SDS and were stored desiccated at 4° C. in plastic wrap.

Other probes designed to study constitutive matrix gene expression were prepared in similar fashion and applied to HMS-1 and HMS-X.

GEL ELECTROPHORESIS

The expression of a number of matrix molecule genes was shown using cross-hybridizing murine cDNA probe for nidogen (Timpl (1983) Eur. J. Biochem. 137:455–465) and human cDNAs for the extracellular matrix molecules B1 and B2 chains of laminin (Timpl et al. J. Biol. Chem. 54:9933–9937), the A1 and A2 chains of type IV collagen (ATCC), the A1 chains of type I and type III collagen (ATCC), fibronectin, and the core proteins of a heparan sulfate proteoglycan (perlecan), Noonan et al., J. Biol. Chem. 266:22939–22947 and chondroitin sulfate proteoglycan. Matrix gene expression was studied with known probes to extracellular matrix molecules by polyA RNA selection and extraction followed by Northern blot gel electrophoresis, according to standard methods. (Sambrook et al., supra)

ESTABLISHMENT OF PROSTATIC CARCINOMA LINES

A series of cultures of primary prostate cancer including Gleason grades 1–5 are established from radical prostatectomy specimens. Prostatic carcinomatous areas are visualized by gross examination of the dissected gland and confirmed by frozen section. The area of the cancer is minced into 1 mm$^3$ fragments and subjected to overnight digestion in 10 ml of dissociating solution which consists of 200 units/ml of collagenase type I (Sigma, St. Louis, MO.) plus 250 g/ml of DNA-ase type I (Sigma) dissolved in RPMI 1640 medium with 10% fetal calf serum. The fragments are digested at 37° C. with gentle agitation. The liberated cell clumps are washed, pelletized and resuspended in KGM selective media with added epidermal growth factor and bovine pituitary extract supplements (GIBCO, Grand Island, N.Y.). The growth of contaminating fibroblasts is suppressed with this media and only epithelial cells grow out of the clumps. After subsequent passage, the population is 100% epithelial which can be verified by positive keratin immunoreactivity and negative vimentin immunoreactivity. Flow cytometric studies are carried out on the cultured cells to determine ploidy.

CULTURING ON HUMATRIX

Pure populations of prostate carcinoma cells, before they exhibit any signs of terminal differentiation (increased size or expression of high molecular weight keratins), are cultured on Humatrix. Humatrix cultures are compared to cultures on plastic. The cells grown on Humatrix are monitored with respect to their proliferation, their immunocytochemical profile, their DNA content, and their PSA secretion as evidence of both their genetic as well as phenotypic stability. Specifically, the ability of Humatrix to retard or prevent terminal differentiation in prostatic carcinoma cells which is inevitable when the cells are cultured on plastic is observed.

PROLIFERATION STUDIES

Initial studies of proliferation include studies of cell culture doubling time. Subsequent studies use two standard approaches: Ki-67 antigen expression and bromodeoxyuridine uptake. A murine monoclonal antibody, Ki-67 (Dako Corporation) which recognizes an as-yet undefined human nuclear epitope present in cells in S, $G_1$, $G_2$, and M, but no $G_0$ is used to study the percentage of cells in the cultured prostatic carcinomas engaged in active proliferation. A second approach involves studies of bromodeoxyuridine uptake. The strategy employs 5-bromo-2'-deoxyuridine (BrdU), a thymidine analog, which is incorporated into replicating DNA and subsequently localized using a specific murine monoclonal antibody to BrdU (Amersham). Only cells in S phase of the cell cycle display nuclear immunoreactivity. The prostatic carcinoma cells growing on Humatrix are labelled. Prostatic carcinoma cells are exposed to thymidine-free media supplemented with bromodeoxyuridine (3 g/ml) for 1–4 hours prior to immunocytochemical analysis.

IMMUNOCYTOCHEMICAL STUDIES

Immunocytochemical studies employ the use of standard murine monoclonal or rabbit polyclonal antibodies to PSA (1/50 dilution), low molecular weight (39,43,50 kd) cytokeratin (1/30 dilution), intermediate molecular weight (34βE12) (58,56.5,56 kd) cytokeratin (1/1000 dilution), vimentin (1/20 dilution), and smooth muscle actin (1/2000 dilution) (DAKO Corporation, Carpinteria, Calif.; Becton-Dickinson, Mountain View, Calif.). The second antibody used in the immunocytochemical studies is an affinity-purified peroxidase-conjugated sheep anti-mouse IgG or goat anti-rabbit IgG (1/200, 1/25 dilutions, respectively). Detection of immunocytochemical positivity is achieved by conjugating peroxidase polymerizing diaminobenzidine (DAB), producing brownish-black staining at sites of antigen presence. The expression of keratins in the prostatic carcinoma cells cultures on Humatrix is monitored over time and compared to routine cultures. A switch in keratin expression, especially to higher molecular weight cytokeratins, suggests phenotypic instability or the beginnings of terminal differentiation.

FLOW CYTOMETRIC STUDIES

For flow cytometric studies, a single nuclear suspension is obtained from monolayer cell cultures grown on either plastic or Humatrix by trypsin digestion, and staining with propidium iodide in the presence of 0.1% Triton X-100, which cells are analyzed on a FACSCAN (Becton Dickinson Immunocytometry Systems, Mountain View, CA). The propidium iodide fluorescence histogram obtained from normal peripheral blood lymphocytes is used to standardize the location of the diploid peak, and additional gating of the forward scatter-side scatter dot plot is used to exclude the contribution of fragmented nuclei. The fluorescence histograms are then analyzed. Flow cytometry and DNA ploidy is used not only to screen the initial cultures but to monitor them over time for genetic stability/instability.

KARYOTYPE ANALYSIS

Karyotype analysis of the lines is carried out periodically by Giemsa-banded staining. The cells are split, plated in fresh media, allowed to attach for 8 hr, and exposed to 1 M colchicine for 4–8 hr. For slower growing partner cells and their fusions, the length of colchicine exposure is lengthened to result in increased numbers of cells arrested in metaphase. After exposure the cells are harvested in 0.1% trypsin-EDTA. The cells are centrifuged at 3000 g for 10 minutes and the pellet resuspended in 0.035 M KCI, 0.5% sodium citrate. The lysed cells are fixed in 2.0% paraformaldehyde for 10 minutes and drops titrated on a microscopic slide and allowed to air dry. The slides are stained with Giesma stain and the mitotic chromosomes examined in a Zeiss Photomicroscope III with a 63 X plan-apo lens and an attached projection screen. The chromosomal spreads are optimized to reveal enough good metaphase preparations to count yet avoid the phenomenon of "chromosome soup". In optimal preparations, 20 chromosomal spreads are counted for each cell line. Mean, range, medium, and modal chromosomal number are calculated. Based predominantly on the modal numbers and ranges as well as the presence of marker chromosomes, whether the cultured prostate carcinoma cells are manifesting genetic stability when cultured on Humatrix compared to routine conditions is determined.

PROSTATIC SPECIFIC ANTIGEN (PSA) SECRETION STUDIES

Cultures are monitored from time to time with respect to PSA secretion. In this regard cells which are anticipated to undergo terminal differentiation after several passages on plastic are compared to cells grown on Humatrix. Prostatic carcinoma cells are seeded in plastic and Humatrix-coated 24 well plates (10$^6$ cells/well). After seeding the prostatic epithelial cells to both uncoated and Humatrix-coated wells and allowing them to attach and grow, conditioned media is collected for 24 hr every other day for 10 days and pooled.

The pooled conditioned media is clarified and concentrated and cell number determined by trypsinizing the cells and counting in a Coulter Counter. PSA levels in conditioned media are determined using the Tandem-R PSA immunoradiometric assay (Kuriyama et al. (1980) Cancer Res. 40:4658–4666). For PSA, 50 µl of conditioned media is added to plastic tubes followed by monoclonal anti-PSA IgG-coated beads and 100 µl of $^{125}$I-labelled anti PSA IgG tracer antibody. The Tandem-R Assay is a solid phase, two-site immunometric assay. Samples containing PSA are reacted with a plastic bead (solid phase) coated with a monoclonal antibody directed toward a unique site on the PSA molecule and, simultaneously, with a radiolabelled monoclonal antibody directed against a distinctly different antigenic site on the same PSA molecule. Following the formation of the solid phase/PSA/labelled antibody sandwich, the bead is washed to remove unbound labelled antibody. The radioactivity bound to the solid phase is measured in a gamma counter. The amount of radioactivity measured is directly proportional to the concentration of PSA present in the test sample, which is determined from a standard curve. The standard curve is based on the concurrent testing of the PSA calibrators from 0 to 100 ng PSA/ml. Using this assay, the samples are incubated for 4 hours, washed (2×) with phosphate-buffered saline and counted in a Picker gamma counter. Cultured prostatic carcinoma cells are monitored periodically for PSA secretion so as to determine their phenotypic stability in Humatrix compared to routine culture conditions. PSA secretion inevitably decreases when prostatic carcinoma cells are cultured on plastic as they undergo terminal differentiation.

PREPARATION OF HUMATRIX a. Xenoplantation of tumor cells and growth of tumor.

The tumor is serially passaged with a trochar. 1 mm$^3$ fragments are placed subcutaneously. Up to four fragments may be introduced into the mouse in the flank and back in accordance with conventional procedures.

b. Extraction of Humatrix, isolation and characterization.

1. Urea/guanidinium-HCl method

Tumors are harvested at 1–2 g of size. A given mouse can support the growth of 4 independent tumors. The tumor is grown in mice rendered lathyritic by feeding them a diet containing β-aminoproprionitrile (BAPN) fumarate. Approximately 10 g of tumor are harvested. Tumors are homogenized in 2 ml/g starting material of a high salt extraction buffer (3.4 M NaCl, 0.05 Tris-HCl, 20 mM EDTA, 10 mM N-ethyl maleimide (NEM), pH 7.4) at 4° C. g. The homogenate is spun for 15 min at 12,000 g at 4° C. and the supernatant is discarded. The previous two steps are repeated twice more. The resulting pellet is extracted overnight at 4° C. with 0.5 ml urea/gdn-HCl extraction buffer per g starting material with stirring (6 M urea, 2 N gdn-HCl, 50 mM Tris-HCl, 20 mM EDTA, 10 mM NEM, pH 7.4 with added 2.0 mM dithiothreitol (DTT)). The extract is spun for 30 min at 24,000 g at 4° C. The supernatant is dialyzed against several changes of Tris buffered saline (TBS) at 4° C. (0.15 M NaCl, 0.05 M Tris-HCl, 20 mM EDTA, 10 mM NEM, pH 7.4). For sterilization, the final dialyses are against 0.5% chloroform, followed by physiologic cell culture media using a dialysis membrane with a cutoff of 5–10 kDa.

Using the above procedure, 0.5 ml of 3 mg/ml Humatrix is obtained from 1 g of HMS-X starting material. Humatrix can be stored frozen at −20° C., is a liquid at 4° C., and undergoes gelation at 25°–37° C. within 1 hr. The integrity of the formed gel is demonstrated by its being impervious to penetration by a loading dye composed of 12.5 g Ficoll, 0.125 g bromophenol blue and 0.125 g xylene cyanol.

2. Pepsin hydrolysis method

Tumors are harvested and homogenized in high salt buffer, the process repeated twice and a pellet obtained as described above. The only difference with this method is that the mice need not be rendered lathyritic and can be fed a normal diet. The pellet is suspended in 5 ml 0.5 N acetic acid per g of starting material. 160 µl of freshly prepared 50 mg/ml pepsin in 0.01 M HCl per g of starting material is added. Extraction occurs overnight at 4° C. with stirring. The extract is spun for 15 min at 3000 g at 4° C. The supernatant is removed and dialyzed against 50 mM Tris, 20 mM EDTA, 10 mM NEM, pH 7.8 overnight at 4° C., The leftover pellet is re-extracted and the steps repeated beginning with the suspension in acetic acid. The dialyzed supernatants are pooled and 240 mg solid NaCl/ml is added. The solution is stirred for 20 hr at 4° C., followed by centrifugation at 17,000 g for 30 min at 4° C. The pellet is resuspended in 0.5 ml 0.5 N acetic acid with 20 mM EDTA and 10 mM NEM and dialyzed against several changes of 0.005 N acetic acid, 0.14 M NaCl, 5 mM KCl, 20 mM EDTA, and 10 m mM NEM at 4° C. For sterilization purposes, the acetic acid substitutes for the chloroform, which was used in the previous extraction method. However, if the acetic acid proves toxic to certain cells, an additional dialysis against media can be used.

The resulting solution is concentrated to 0.25 ml final volume per g of starting material (or any volume which yields at least 1 mg/ml final protein concentration) by ultrafiltration at 4° C. (A microcon-10 microconcentrator with a 10 kDa molecular weight cut-off can be used; a centricon-10 could be used for larger amounts and a centriprep-10 for even larger volumes.)

Using the pepsin hydrolysis method, 0.25 ml of 1 mg/ml Humatrix is obtained from 1 g of HMS-X starting material. The product has the properties described for the urea/gdn-HCl preparation.

HMS-1 GROWTH AND CULTURE

HMS-1 was established directly from a patient's tumor with histopathological features of a basal cell adenocarcinoma, a subtype of adenoidcystic carcinoma in keratinocyte growth media (KGM) (GIBCO, Grand Island, N.Y.) supplemented with manufacturer amounts of recombinant EGF and bovine pituitary extract. They were shown to be Mycoplasma-free by direct culture in indirect Hoechst DNA staining, as well as by electron microscopy. The line exhibited immortality and a stable phenotype, having a stable karyotype and phenotype unchanged for over 100 passages with a population doubling time of approximately 24 h. The line is split from 1:3 to 1:5 with trypsin: EDTA. Antibodies specific for low molecular weight cytokeratins (39, 43, 50 kDa and smooth muscle actin (DAKO Corporation, Carpinteria, CA; Becton Dickinson, Mountain View, CA) showed the cells to be immunoreactive to these antibodies, indicating the myoepithelial nature of HMS-1. Employing antibodies specific for laminin and type IV collagen, approximately 30% of the cells were positively immunostained. Ultrastructural examination revealed microvilli and parallel arrays of microfilaments (thin filaments, dual structures of a myoepithelial phenotype). Monolayer cultures in KGM, grown as described above, reveal the presence of a scant basal extracellular electron dense matrix and the complete absence of cell-to-cell attachments (desmosomes).

In cultures comprising HMS-1 cells, in the media described above to which 10% FCS was added, after 5–7 days, the cells underwent growth arrest at lower cell density than in the absence of FCS, a change in growth pattern to island morphology, and epithelial differentiation, which was reflected in the acquisition of numerous desmosomes. The cell line underwent terminal differentiation and serum after several doublings, which required 12–14 days (see Graph B enclosed).

Chromosome analysis of HMS-1 grown in the absence of serum carried out by Giemsa-banded staining of metaphase spreads at passages 2, 30 and 55 revealed an essentially diploid modal chromosome count of 46–47 (range 45–50). Common karyotypic changes were the loss of chromosomes 6 and 22, an abnormal chromosome 8q, and a rearranged marker chromosome, t(6;9) (p11.2; p13). There was also a gain of an extra chromosome 20 between passages 2 and 30. DNA ploidy analysis of several early passages (passage 2 days) and late passages (passage 30 days; passage 55 days) by flow cytometry confirmed the stable diploid nature of the line]

HMS-X GROWTH

Fresh tissue from the tumor supplying HMS-1 (1 mm$^3$ sized fragments were implanted subcutaneously via trochar into the flank and back of athymic nude mice (BALB/c) Mice were kept in aseptic housing in a laminar flow room. Bedding, food and water were all sterilized. When tumors reached 1–2 cm in greatest diameter, 1 mm$^3$ explants were passed to subsequent mice. The original surgical specimen was a white to tan, multinodular mass exhibiting cylandromatous and cribriforming histologic patterns with abundant acellular matrix deposits as well as squamous metaplastic changes within invasion islands. The transplanted xenograft exhibits gross appearance similar to that of the original tumor as evidenced by gross, routine microscopic immunocytochemical staining and ultrastructural studies. The xenograft retained an abundant eosinophilic extracellular matrix which stained strongly with alcian blue and periodic acid-Schiff stains. The latter stain was shown to be diastase-sensitive by pre-digesting with diastase and abolishing staining supporting the presence of glycosylated matrix molecules other than mucin, e.g. proteoglycans. From earliest xenograft passage the extracellular matrix comprised approximately 50% of the tumor volume. The extracellular matrix exhibited strong immunoperoxidase staining for laminin (please give reference). Electron microscopy revealed tumor cell islands surrounded by an abundant ground substance-like matrix which lack periodic cross-banded fibers and resemble the ultrastructural appearance of Matrigel (EHS) tumor matrix.

RESULTS

DNA fingerprint profiles using single and multi-locus hypervariable probes (pYNH24 and 33.6) were identical for the xenograft in each of three passages of the cell line and demonstrated a novel band pattern differing from that of HeLa cells and a negligible DNA contribution from murine cells. There was no evidence of a murine DNA component by flow analysis, nor by the DNA fingerprint profiles, establishing the human origin of the cells.

The proteins being expressed were determined using cDNA probes for a number of basement membrane mRNAs. Gene expression of the matrix molecules type IV collagen; type I collagen, heparan sulfate proteoglycan chondroitin sulfate proteoglycan, nidogen and laminin including either 1, 2 or 3 chains was considerably greater for HMS-X, than for HMS-1 and HMS-XC, the primary exception being the fibronectin gene, being 20-fold greater for HMS-1 than HMS-X. A comparison of the in vitro effects of serum on extracellular matrix gene expression of HMS-1 compared to HMS-X was performed demonstrating that the expression between the two cells lines was still quantitatively and qualitatively different. Levels of extracellular matrix gene expression were determined by Northern blot gel electrophoresis and compared. HMS-X still expressed extracellular matrix transcripts at higher levels than serum-treated HMS-1 except for fibronectin and heparan sulfate proteoglycan.

Attempts to engraft HMS-1 in athymic (nude) or SCID mice failed. The cell line HMS-XC also failed to form tumors upon grafting in the same mice. HMS-X failed to grow xenografts after removal of the supporting extracellular matrix from the tumor explant by mechanical and enzymatic dissociation and subsequent reinjection of the washed cells, despite their ability to grow in culture. The conclusion from these results is that HMS-X, HMS-1 and HMS-XC are obligately matrix dependent for their tumorigenicity. When HMS-1 was grown on the surface of Matrigel, glandular differentiation occurred; however, when HMS-1 was suspended 1:1 into liquid Matrigel according to manufacturer's recommendation and injected into athymic mice no tumors emerged in athymic mice from 20 injection sites (5 mice) after periods of up to six months. However, when HMS-1 was mixed with Humatrix, there was a 40% rate of emerging tumors (tumorigenicity).

It is evident from the above results, that novel human basement-like compositions can be provided which may be used for a variety of purposes, such as studying interactions between basement membrane and cells, growing cells in culture and in vivo, particularly fastidious tumor cells, extracting components individually or in combination from the basement membrane as a source of these components, and the like. In addition, cells are provided which can be used for studying basement membrane component expression, response to various agents affecting the basement membrane expression, and the like. By being able to grow tumor cells in culture and in vivo, the tumor cells can also be investigated as to their response to various agents, so that effective chemotherapy may be developed, drugs may be screened, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for growing human tumorigenic cells in an immunocompromised mammal host, said method comprising:

introducing said tumorigenic cells into said mammal host mixed with a basement membrane like composition derived from basement membrane produced by HMS-X cells and comprising from 20–30 weight % heparan/chondroitin sulfate proteoglycan, from about 10–20 weight % fibronectin, 2–10 weight % laminin, about 10 weight % nidogen/entactin and from about 2–10 weight % of each of type I and IV collagen; and growing said mammal host for sufficient time for said tumorigenic cells to grow.

2. A method according to claim 1, wherein said mammal host is a mouse.

3. A method according to claim 1, wherein said composition is produced by:

extracting an homogenized xenograft of human basement membrane producing tumorigenic cells with a high salt concentration solution and isolating the solids from said extract;

extracting said solids with at least one of a chaotropic medium and pepsin hydrolysis and isolating the liquid fraction; and dialyzing the liquid fraction with aqueous chloroform or acetic acid.

* * * * *

UNITED STATES PATENT AND TRADEMARK OFFICE
CERTIFICATE OF CORRECTION

PATENT NO.   : 5,508,188
DATED        : April 16, 1996
INVENTOR(S)  : BARSKY, et al.

It is certified that error appears in the above-indentified patent and that said Letters Patent is hereby corrected as shown below:

Col. 1, line 8, immediately preceding BACKGROUND OF THE INVENTION, insert a new paragraph to read --This invention was made with Government support under Grant No's.: CA 40225; CA 71195; CA 01351, awarded by the National Institutes of Health. The Government has certain rights in this invention.--.

Signed and Sealed this

Sixth Day of April, 1999

Attest:

Q. TODD DICKINSON

Attesting Officer

Acting Commissioner of Patents and Trademarks